(12) United States Patent
Person (10) Patent No.: US 7,744,530 B2
(45) Date of Patent: *Jun. 29, 2010

(54) SURGICAL INSTRUMENT HOLDER

(75) Inventor: Wayne C. Person, Newtown, CT (US)

(73) Assignee: Tyco Healthcare Group LP, North Haven, CT (US)

(*) Notice: Subject to any disclaimer, the term of this patent is extended or adjusted under 35 U.S.C. 154(b) by 192 days.

This patent is subject to a terminal disclaimer.

(21) Appl. No.: 11/977,195

(22) Filed: Oct. 24, 2007

(65) Prior Publication Data

US 2008/0132767 A1 Jun. 5, 2008

Related U.S. Application Data

(63) Continuation of application No. 10/647,950, filed on Aug. 26, 2003, now Pat. No. 7,294,104, which is a continuation of application No. 09/779,021, filed on Feb. 7, 2001, now Pat. No. 6,610,009, which is a continuation of application No. 09/235,593, filed on Jan. 22, 1999, now Pat. No. 6,200,263.

(60) Provisional application No. 60/072,406, filed on Jan. 23, 1998.

(51) Int. Cl.
*A61N 1/32* (2006.01)

(52) U.S. Cl. ........................ 600/227; 600/234

(58) Field of Classification Search ................ 600/231, 600/227, 229, 234, 210, 228, 230, 235, 201; 403/385, 389
See application file for complete search history.

(56) References Cited

U.S. PATENT DOCUMENTS

| | | |
|---|---|---|
| 373,362 A | 11/1887 | Hamilton |
| 497,064 A | 5/1893 | Van Meter |
| 601,523 A | 3/1898 | Orchard |
| 1,157,202 A | 10/1915 | McLeland |
| 1,400,616 A | 12/1921 | Pearson |
| 1,706,500 A | 3/1929 | Smith |
| 1,707,689 A | 4/1929 | Sloan |
| 1,839,726 A | 1/1932 | Arnold |
| 1,919,120 A | 7/1933 | O'Connor |
| 1,963,173 A | 6/1934 | Morin |
| 2,053,868 A | 9/1936 | Grosso |
| 2,384,304 A | 9/1945 | Helfrick |

(Continued)

FOREIGN PATENT DOCUMENTS

DE 8702192.7 6/1987

(Continued)

OTHER PUBLICATIONS

"Pilling Surgical Instruments" brochure by Pilling, A Rusch International Company 1993.

*Primary Examiner*—Pedro Philogene (57) ABSTRACT

An apparatus for holding a surgical instrument relative to a base is provided having a mounting portion configured and dimensioned to engage a portion of a base, a jaw assembly including first and second jaw members which define a retaining area therebetween configured and dimensioned to retain the shaft of a surgical instrument therein and thereby fix the length of the instrument shaft relative to the base and an operative site, and an instrument position adjustment mechanism which includes an adjustment member rotatably disposed in relative to the mounting portion to facilitate selective position adjustment of the jaw assembly with respect to the mounting portion.

10 Claims, 9 Drawing Sheets

U.S. PATENT DOCUMENTS

| | | |
|---|---|---|
| 2,473,266 A | 6/1949 | Wexler |
| 2,510,198 A | 6/1950 | Tesmer |
| 2,594,086 A | 4/1952 | Smith |
| 2,623,517 A | 12/1952 | Barlow |
| 2,670,732 A * | 3/1954 | Nelson ................ 600/234 |
| 2,701,562 A | 2/1955 | Michael et al. |
| 3,070,088 A | 12/1962 | Brahos |
| 3,129,706 A | 4/1964 | Reynolds, Jr. |
| 3,168,093 A | 2/1965 | Gauthier |
| 3,384,077 A | 5/1968 | Gauthier |
| 3,463,144 A | 8/1969 | Hammond |
| 3,509,873 A | 5/1970 | Karlin et al. |
| 3,522,799 A | 8/1970 | Gauthier |
| 3,680,546 A | 8/1972 | Asrican |
| 3,724,449 A | 4/1973 | Gauthier |
| 3,747,592 A | 7/1973 | Santos |
| 3,749,088 A | 7/1973 | Gauthier |
| 3,858,578 A | 1/1975 | Milo |
| 3,965,890 A | 6/1976 | Gauthier |
| 3,998,217 A | 12/1976 | Trumbull |
| 4,010,741 A | 3/1977 | Gauthier |
| 4,048,987 A | 9/1977 | Hurson |
| 4,165,746 A | 8/1979 | Burgin |
| 4,190,042 A | 2/1980 | Sinnreich |
| 4,226,228 A | 10/1980 | Shin et al. |
| 4,254,763 A | 3/1981 | McCready |
| 4,281,366 A | 7/1981 | Wurster et al. |
| 4,337,762 A | 7/1982 | Gauthier |
| 4,421,107 A | 12/1983 | Estes |
| 4,421,108 A | 12/1983 | Cabrera |
| 4,424,724 A | 1/1984 | Bookwalter |
| 4,430,991 A | 2/1984 | Darnell |
| 4,457,300 A | 7/1984 | Budde |
| 4,467,791 A | 8/1984 | Cabrera |
| 4,492,229 A | 1/1985 | Grunwald |
| 4,562,832 A | 1/1986 | Wilder et al. |
| 4,573,452 A | 3/1986 | Greenberg |
| 4,597,030 A | 6/1986 | Brody et al. |
| 4,605,990 A | 8/1986 | Wilder et al. |
| 4,617,916 A | 10/1986 | Levahn et al. |
| 4,627,421 A | 12/1986 | Symbas et al. |
| 4,702,230 A | 10/1987 | Pelta |
| 4,726,356 A | 2/1988 | Santilli et al. |
| 4,744,363 A | 5/1988 | Hasson |
| 4,745,908 A | 5/1988 | Wardle |
| 4,747,395 A | 5/1988 | Brief |
| 4,765,311 A | 8/1988 | Kulik et al. |
| 4,782,819 A | 11/1988 | Adair |
| 4,796,846 A | 1/1989 | Meier et al. |
| 4,813,401 A | 3/1989 | Greishaber |
| 4,829,985 A | 5/1989 | Bouetil |
| 4,848,323 A | 7/1989 | Marijnissen et al. |
| 4,852,552 A | 8/1989 | Chaux |
| 4,856,518 A | 8/1989 | McFadden |
| 4,865,019 A | 9/1989 | Phillips |
| 4,867,404 A | 9/1989 | Harrington et al. |
| 4,870,952 A | 10/1989 | Martinez |
| 4,921,326 A | 5/1990 | Wild et al. |
| RE33,234 E | 6/1990 | Landry |
| 4,932,395 A | 6/1990 | Mehdizadeh |
| 4,949,707 A | 8/1990 | Levahn et al. |
| 4,988,355 A | 1/1991 | Leveen et al. |
| 5,000,163 A | 3/1991 | Ray et al. |
| 5,003,434 A | 3/1991 | Gonser et al. |
| 5,025,779 A | 6/1991 | Bugge |
| 5,049,153 A | 9/1991 | Nakao et al. |
| 5,052,373 A | 10/1991 | Michelson |
| 5,052,374 A | 10/1991 | Alvarez-Jacinto |
| 5,067,477 A | 11/1991 | Santangelo |
| 5,088,472 A | 2/1992 | Fakhrai |
| 5,100,430 A | 3/1992 | Avellanet et al. |
| 5,133,727 A | 7/1992 | Bales et al. |
| 5,152,279 A | 10/1992 | Wilk |
| RE34,150 E | 12/1992 | Santilli |
| 5,167,223 A | 12/1992 | Koros et al. |
| 5,176,129 A | 1/1993 | Smith |
| 5,195,505 A | 3/1993 | Josefsen |
| 5,197,971 A | 3/1993 | Bonutti |
| 5,224,680 A | 7/1993 | Greenstein et al. |
| 5,228,451 A | 7/1993 | Bales et al. |
| 5,231,974 A | 8/1993 | Giglio et al. |
| 5,235,966 A | 8/1993 | Jamner |
| 5,238,002 A | 8/1993 | Devlin et al. |
| 5,254,130 A | 10/1993 | Poncet et al. |
| 5,271,385 A | 12/1993 | Bailey |
| 5,284,130 A | 2/1994 | Ratliff |
| 5,297,538 A | 3/1994 | Daniel |
| 5,299,563 A | 4/1994 | Seton |
| 5,306,234 A | 4/1994 | Johnson |
| 5,325,866 A | 7/1994 | Krzyzanowski |
| 5,336,221 A | 8/1994 | Anderson |
| 5,337,735 A | 8/1994 | Salerno |
| 5,346,504 A | 9/1994 | Ortiz et al. |
| 5,351,168 A | 9/1994 | Easley |
| 5,354,311 A | 10/1994 | Kambin et al. |
| 5,370,109 A | 12/1994 | Cuny |
| 5,375,481 A | 12/1994 | Cabreara et al. |
| 5,380,338 A | 1/1995 | Christian |
| 5,381,788 A | 1/1995 | Matula et al. |
| 5,386,489 A | 1/1995 | Stokes |
| 5,400,774 A | 3/1995 | Villalta et al. |
| 5,411,481 A | 5/1995 | Allen et al. |
| 5,419,339 A | 5/1995 | Palmer |
| 5,429,121 A | 7/1995 | Gadelius |
| 5,441,042 A | 8/1995 | Putman |
| 5,441,044 A | 8/1995 | Tovey et al. |
| 5,447,149 A | 9/1995 | Kikawada et al. |
| 5,450,293 A | 9/1995 | Hoffman |
| 5,450,842 A | 9/1995 | Tovey et al. |
| 5,452,395 A | 9/1995 | Schichman et al. |
| 5,452,733 A | 9/1995 | Sterman et al. |
| 5,500,918 A | 3/1996 | Pileski et al. |
| 5,503,617 A | 4/1996 | Jako |
| 5,514,077 A | 5/1996 | Rabban |
| 5,520,610 A | 5/1996 | Giglio et al. |
| 5,520,611 A | 5/1996 | Rao et al. |
| 5,520,678 A | 5/1996 | Heckele et al. |
| 5,535,754 A | 7/1996 | Doherty |
| 5,571,136 A | 11/1996 | Weaver |
| 5,578,056 A | 11/1996 | Pauldrach |
| 5,580,147 A | 12/1996 | Salerno |
| 5,602,948 A | 2/1997 | Currie |
| 5,624,432 A | 4/1997 | Angelchik |
| 5,651,378 A | 7/1997 | Matheny et al. |
| 5,656,012 A | 8/1997 | Sienkiewicz |
| 5,667,472 A | 9/1997 | Finn et al. |
| 5,667,473 A | 9/1997 | Finn et al. |
| 5,667,478 A | 9/1997 | McFarlin et al. |
| 5,727,569 A | 3/1998 | Benetti et al. |
| 5,730,757 A | 3/1998 | Benetti et al. |
| 5,749,892 A | 5/1998 | Vierra et al. |
| 5,755,660 A | 5/1998 | Tyagi |
| 5,782,753 A | 7/1998 | DeFonzo et al. |
| 5,803,902 A | 9/1998 | Sienkiewicz et al. |
| 5,807,243 A | 9/1998 | Vierra et al. |
| 5,823,956 A | 10/1998 | Roth et al. |
| 5,829,447 A | 11/1998 | Stevens et al. |
| 5,836,311 A | 11/1998 | Borst et al. |
| 5,855,614 A | 1/1999 | Stevens et al. |
| 5,857,965 A | 1/1999 | Rootman et al. |
| 5,865,730 A | 2/1999 | Fox et al. |
| 5,875,782 A | 3/1999 | Ferrari et al. |
| 5,879,291 A | 3/1999 | Kolatoa et al. |
| 5,882,299 A | 3/1999 | Rastegar et al. |

| | | | | | | |
|---|---|---|---|---|---|---|
| 5,885,236 A | 3/1999 | Varn | | 6,228,024 B1 | 5/2001 | Co et al. |
| 5,885,238 A | 3/1999 | Stevens et al. | | 6,264,605 B1 | 7/2001 | Scirica et al. |
| 5,888,247 A | 3/1999 | Benetti | | 6,306,085 B1 | 10/2001 | Farascioni |
| 5,891,017 A | 4/1999 | Swindle et al. | | 6,537,212 B2 | 3/2003 | Sherts et al. |
| 5,894,843 A | 4/1999 | Benetti et al. | | 6,565,508 B2 | 5/2003 | Scirica et al. |
| 5,899,425 A | 5/1999 | Corey, Jr. et al. | | 6,610,009 B2 * | 8/2003 | Person ............ 600/234 |
| 5,908,382 A | 6/1999 | Koros et al. | | 6,709,389 B2 | 3/2004 | Farascioni et al. |
| 5,913,818 A | 6/1999 | Co et al. | | 6,733,445 B2 | 5/2004 | Sherts et al. |
| D411,883 S | 7/1999 | Farascioni et al. | | 7,294,104 B2 * | 11/2007 | Person ............ 600/227 |
| 5,921,996 A | 7/1999 | Sherman | | | | |
| 5,927,284 A | 7/1999 | Borst et al. | | | | |
| 5,947,896 A | 9/1999 | Shert et al. | | | | |

FOREIGN PATENT DOCUMENTS

| | | |
|---|---|---|
| 5,967,973 A * | 10/1999 | Sherts et al. ............ 600/233 |
| 5,967,974 A | 10/1999 | Nicholas et al. |
| D417,276 S | 11/1999 | DeFonzo |
| 5,976,080 A | 11/1999 | Farascioni |
| 5,984,867 A | 11/1999 | Deckman et al. |
| 6,007,486 A | 12/1999 | Hunt et al. |
| 6,013,027 A | 1/2000 | Khan et al. |
| D420,130 S | 2/2000 | Nicholas et al. |
| 6,030,340 A | 2/2000 | Maffei et al. |
| 6,033,361 A | 3/2000 | Co et al. |
| 6,102,853 A | 8/2000 | Scirica et al. |
| 6,102,854 A * | 8/2000 | Cartier et al. ............ 600/228 |
| 6,196,968 B1 | 3/2001 | Rydin et al. |
| 6,200,263 B1 * | 3/2001 | Person ............ 600/227 |
| 6,213,940 B1 | 4/2001 | Sherts et al. |

| | | |
|---|---|---|
| EP | 0167345 | 1/1986 |
| EP | 0246086 | 11/1987 |
| EP | 0336526 | 10/1989 |
| EP | 0791329 | 8/1997 |
| EP | 0791330 | 8/1997 |
| EP | 0792620 | 9/1997 |
| FR | 1005345 | 4/1952 |
| GB | 2102681 | 2/1983 |
| IN | 116547 | 6/1918 |
| RU | 938967 | 8/1980 |
| WO | WO 89/04145 | 5/1989 |
| WO | WO 92/21296 | 12/1992 |
| WO | WO 95/17127 | 6/1995 |
| WO | WO 97/10753 | 3/1997 |

* cited by examiner

SURGICAL INSTRUMENT HOLDER

CROSS REFERENCE TO RELATED APPLICATION

This application is a continuation of U.S. application Ser. No. 10/647,950 filed on Aug. 26, 2003 now U.S. Pat. No. 7,294,104 which is a continuation of U.S. application Ser. No. 09/779,021 filed on Feb. 7, 2001 now U.S. Pat. No. 6,610,009 which is a continuation of U.S. application Ser. No. 09/235,593 filed on Jan. 22, 1999 now U.S. Pat. No. 6,200,263 which claims priority to U.S. Provisional Application Ser. No. 60/072,406 filed on Jan. 23, 1998, the contents of which are hereby incorporated by reference in their entirety.

BACKGROUND

1. Technical Field

The subject disclosure relates to minimally invasive surgical procedures and apparatus, and more particularly to apparatus for holding surgical instrumentation during surgery associated with the thoracic cavity.

2. Background of Related Art

It is well established that the performance of various types of surgical procedures using less invasive techniques and instrumentation has provided numerous physical benefits to the patient while reducing the overall cost of such procedures. One area, for example, which has experienced a great increase in the performance of less invasive procedures is in the area of heart surgery. In particular, coronary artery bypass graft (CABG) procedures have been performed using less invasive techniques with much success.

Access to the patient's thoracic cavity for such procedures in the past was typically achieved by a large longitudinal incision in the chest. This procedure, referred to as a median sternotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extended and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating window. The retractor includes a rigid frame and a translation frame slidably connected to the rigid frame. Lower and upper blades are rotatably mounted to the rigid frame and the translation frame respectively. Such a "window" approach requires instrumentation that can be inserted into and manipulated within the limited space available in and around the surgical site.

Therefore, a continuing need exists for more versatile and varied surgical instrumentation which facilitates performing surgical procedures in limited access cavities of a patient during less invasive surgical procedures. A need also exists for instrument holding apparatus to retain surgical instruments in place during surgical procedures and free the surgeons hands.

SUMMARY

The present disclosure addresses the above-noted needs while providing various embodiments of an apparatus for holding surgical instruments that have many unique features and advantages over the prior instrumentation. The presently disclosed apparatus for holding surgical instruments provides greater versatility during surgical procedures which are less invasive than traditional procedures.

For example, in one embodiment, the present disclosure provides an apparatus for holding a surgical instrument relative to a base, which includes a mounting portion configured and dimensioned to engage a portion of a base, a jaw assembly including first and second jaw members which define a retaining area therebetween configured and dimensioned to retain the shaft of a surgical instrument therein and thereby fix the length of the instrument shaft relative to the base and an operative site, and an instrument position adjustment mechanism which includes an adjustment member rotatably disposed in relative to the mounting portion to facilitate selective position adjustment of the jaw assembly with respect to the mounting portion.

The instrument position adjustment mechanism may include a lock member such that when positioned in a locked position, the adjustment member is prevented from moving relative to the mounting portion and when the lock member is positioned in an unlocked position, the adjustment member is permitted to move relative to the mounting portion. The jaw assembly preferably includes a jaw approximation control member which controls movement of one of the first and second jaw members relative to the other of the first and second jaw members.

BRIEF DESCRIPTION OF THE DRAWINGS

Various preferred embodiments are described herein with reference to the drawings, wherein.

DETAILED DESCRIPTION OF PREFERRED EMBODIMENTS

Figure 1:
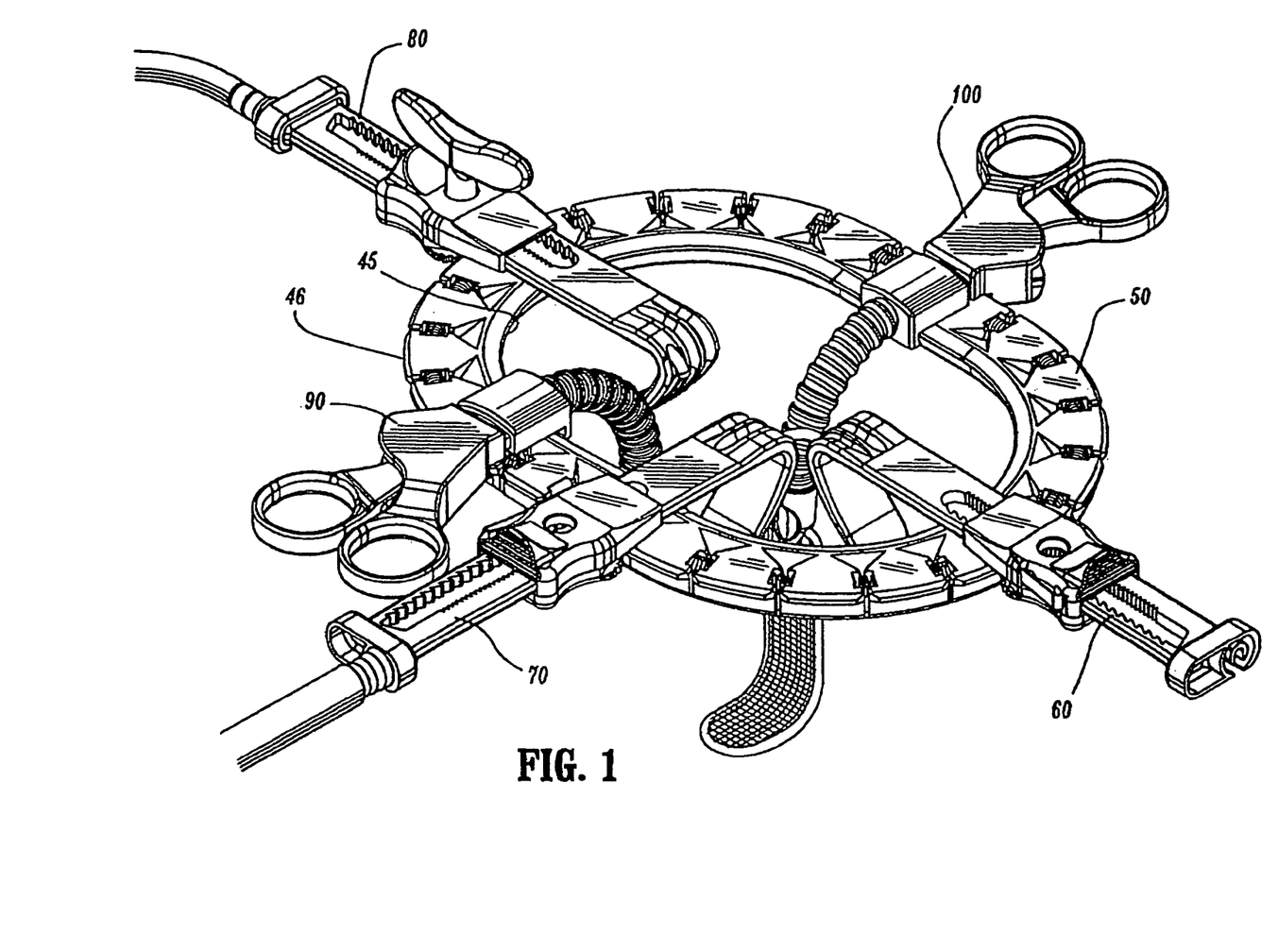
FIG. 1 is a perspective view of a surgical retraction system incorporating a variety of retractors, a heart manipulator and a heart stabilizer, all positioned on a base.

The instrument mounting holder of the present disclosure is designed to mount various accessory instruments to the ring base disclosed in U.S. patent application Ser. No. 08/718,283, filed Sep. 20, 1996, the entire contents of which are incorporated herein by reference. FIG. 1 is a drawing from the '283 patent application and shows a base 50, retractors 60, 70 and 80, a heart stabilizer 90 and a heart manipulator 100. A detailed description of these instruments, how they are mounted to the base 50, and their surgical function is disclosed in the '283 application.

The present disclosure is directed to an instrument holding apparatus, which is removably positionable on base 50, and can mount a variety of instruments such as an illumination instrument, a grasper, a retractor, a heart stabilizer or any other instrument that would be useful in performing the surgical procedure. Only the shaft of the accessory instrument is shown in the drawings and is represented generically by reference letter "S".

Figure 2:
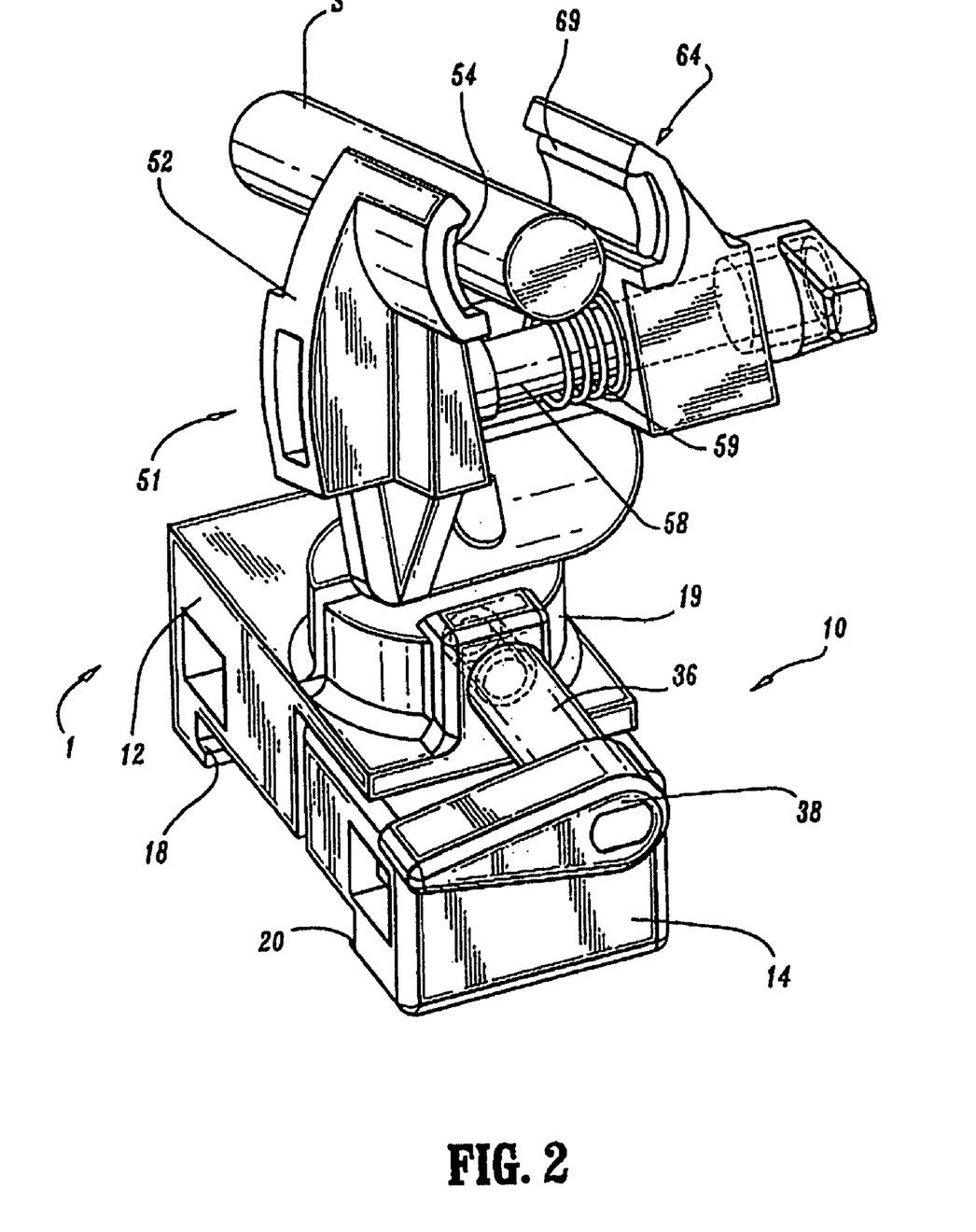
FIG. 2 is a perspective view of the instrument holder of the present disclosure showing an instrument shaft retained in the horizontal position and the jaws in the open position.
Figure 3:
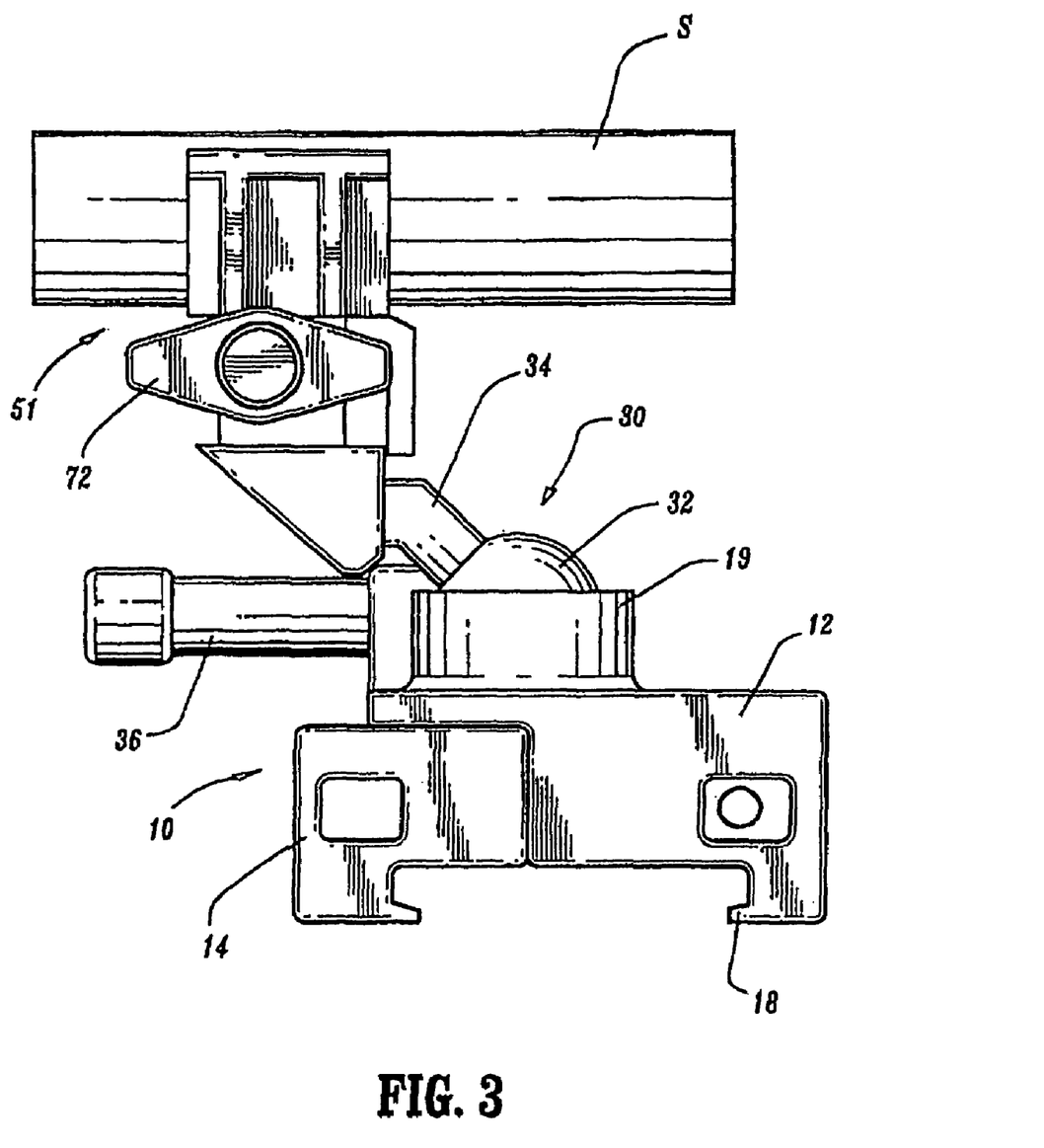
FIG. 3 is a side view of the instrument holder in the position of FIG. 2.
Figure 4:
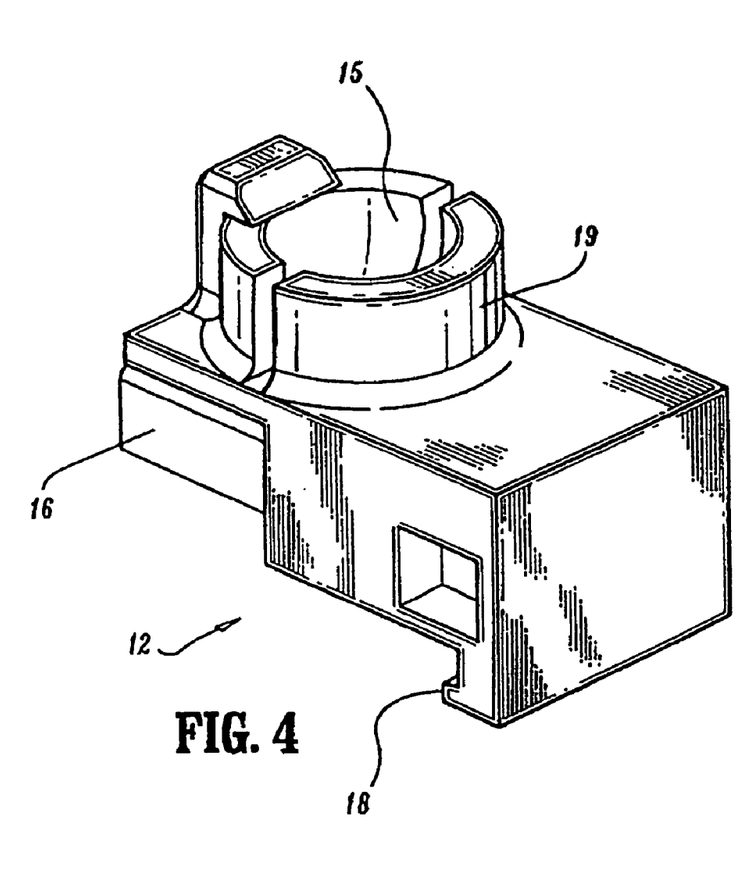
FIG. 4 is a perspective view of a first section of a base mounting assembly of the present disclosure.
Figure 5:
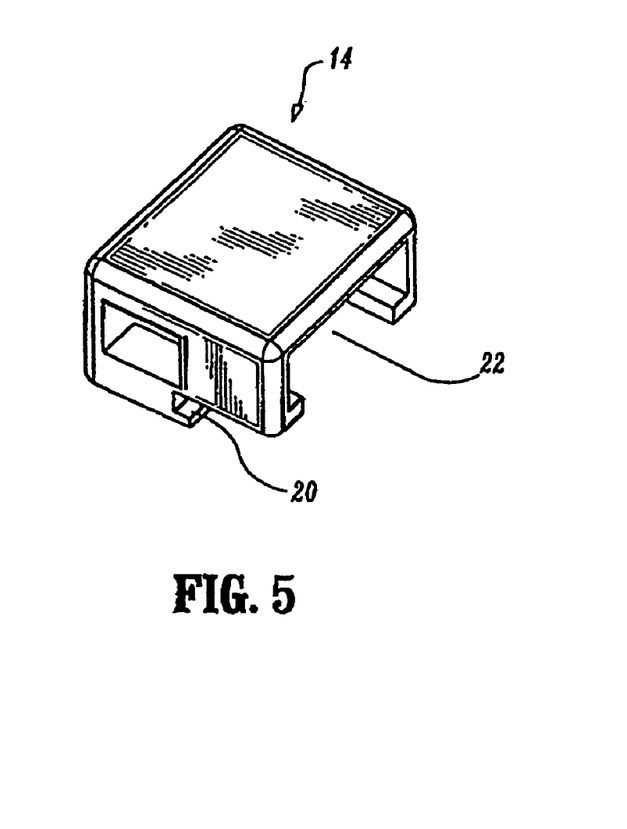
FIG. 5 is a perspective view of a second section of the base mounting assembly.

Referring to FIGS. 1-5, instrument holder 1 includes a mounting portion, such as a base mounting assembly 10 composed of a first section 12 and a second section 14, an instrument position adjustment mechanism 30, and a jaw assembly 51 for supporting the instrument shaft S. As best shown in FIG. 4, first section 12 includes a neck 19 having a socket 15 formed therein for receiving a ball 32, described below. A lip 18 is formed to hook around a front edge 45, FIG. 1, of base 50. An extension 16 extends through a groove 22 formed in second section 14, shown in FIG. 5. A lip 20 of second section 14 is configured to mount to an outer edge 46 of base 50. A biasing spring, not shown, is attached at one end to first section 12 and at the opposite end to second section 14 to help retain the sections 12 and 14 together while allowing first section 12 and second section 14 to be pulled slightly away from each other, against the force of the spring, to facilitate mounting to and release from base 50.

Figure 6:
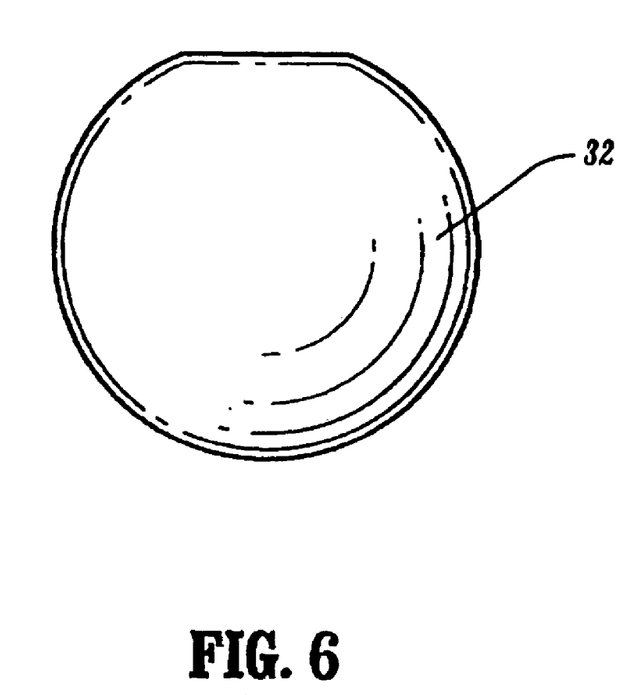
FIG. 6 illustrates the ball for enabling maneuverability of the jaw assembly.
Figure 7:
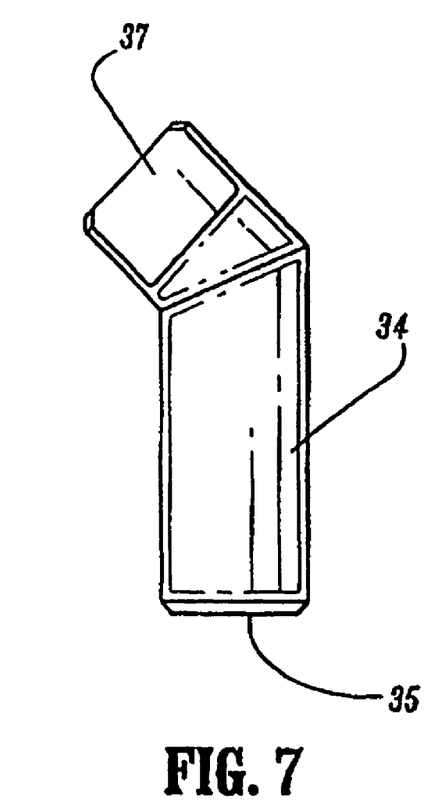
FIG. 7 illustrates a side view of the shaft which is connected at one end to the ball and at the opposite end to the jaw assembly.
Figures 8, 9, 10:
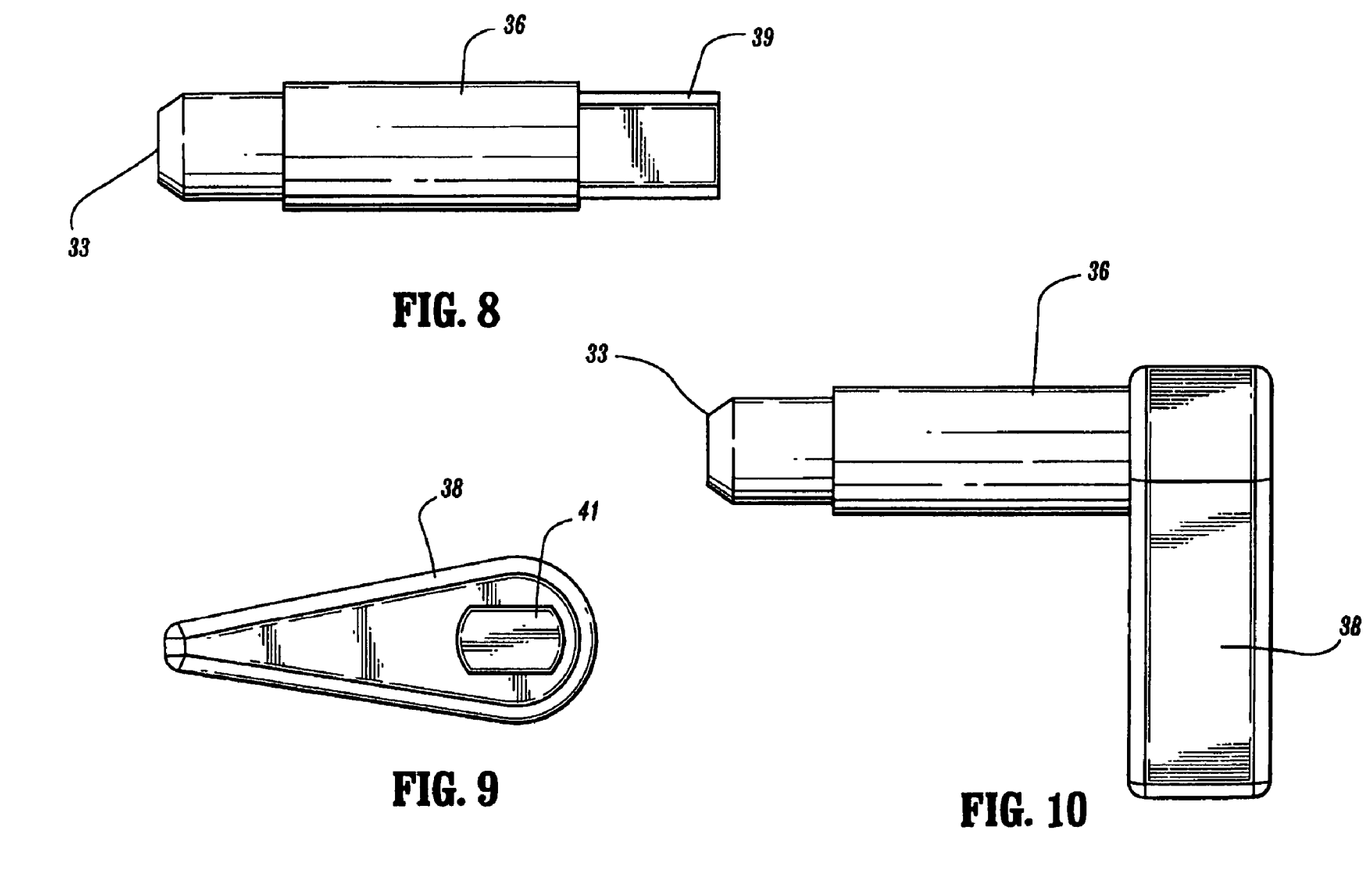
FIG. 8 is a side view of the locking screw which retains the ball in a fixed position.
FIG. 9 illustrates the handle which attaches to the locking screw for rotating the screw.
FIG. 10 is a side view showing the handle attached to the locking screw to form a ball locking assembly.
Figure 11:
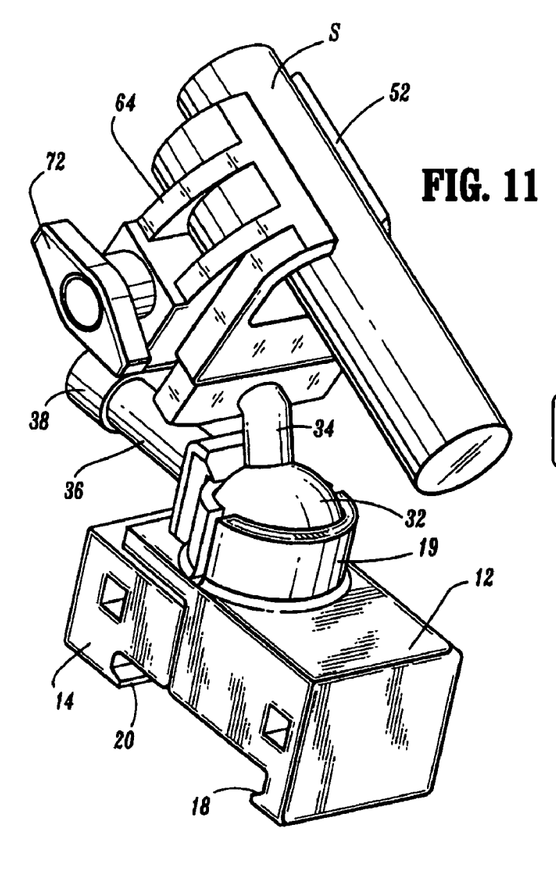
FIG. 11 is a perspective view illustrating the instrument holder with the jaws in the closed position and maneuvered to hold the instrument shaft at an angle.
Figure 12:
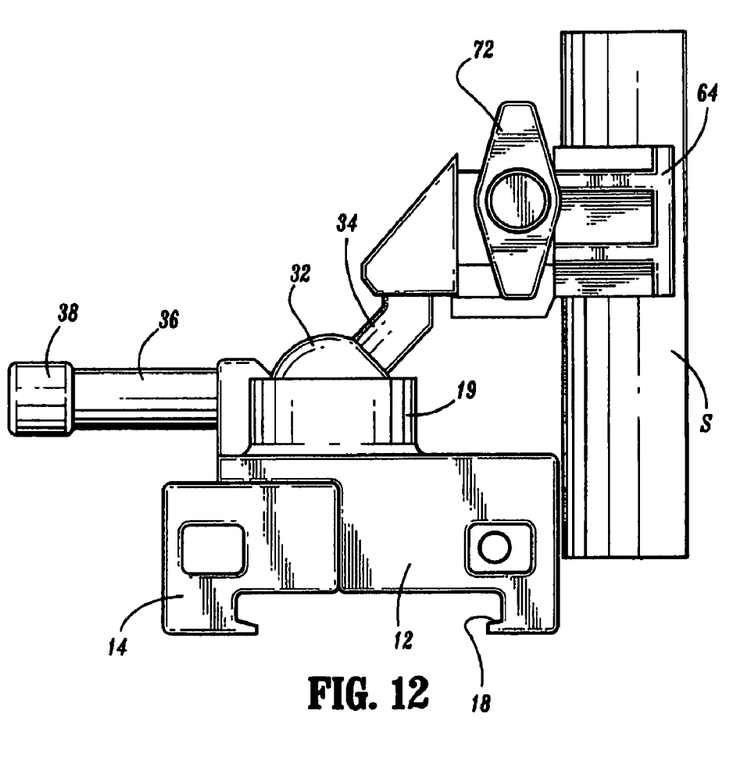
FIG. 12 is a side view illustrating the instrument holder maneuvered to position the instrument shaft perpendicular to the base of the retraction system.

Referring to FIGS. 6-12, position adjustment mechanism 30 includes a ball 32, FIG. 6, a ball shaft 34, FIG. 7, a lock member such as locking screw 36, FIGS. 8 and 10, and a locking screw handle 38, FIGS. 9 and 10. Ball 32 is attached to end 35 of ball shaft 34. Alternatively, ball 32 and shaft 34 could be integral. End 37 of ball shaft 34 is attached to jaw assembly 51. Ball 32 is maneuverable by rotational and pivotal movement through a multitude of positions within neck 19 in order to maneuver the jaws to position the shaft S (and associated instrument) in a variety of orientations. Such maneuverability is shown for example by comparing FIGS. 3, 11 and 12. Once the jaw assembly 51 is maneuvered to the desired position, handle 38, which is attached to locking screw 36 via arm 39 extending through aperture 41, is rotated to advance locking screw 36 so that abutment end 33 tightly presses against ball 32. This locks ball 32 in position and prevents movement thereof.

Figure 13A:
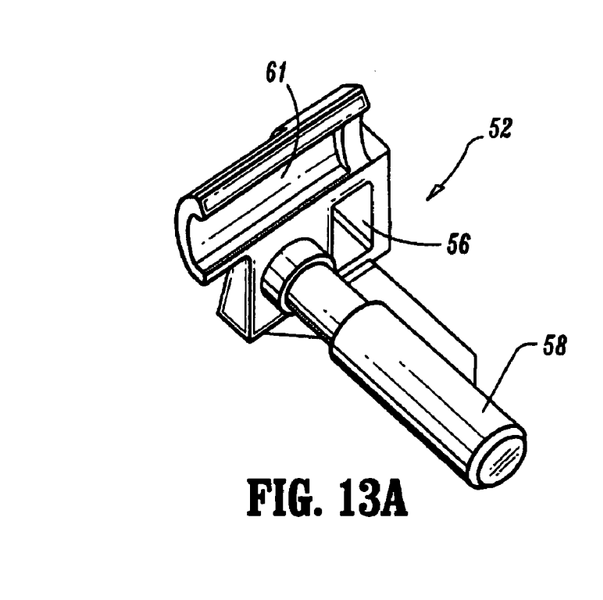
FIGS. 13A and 13B are perspective and side views, respectively, of the stationary jaw for holding the instrument shaft.
Figure 13B:
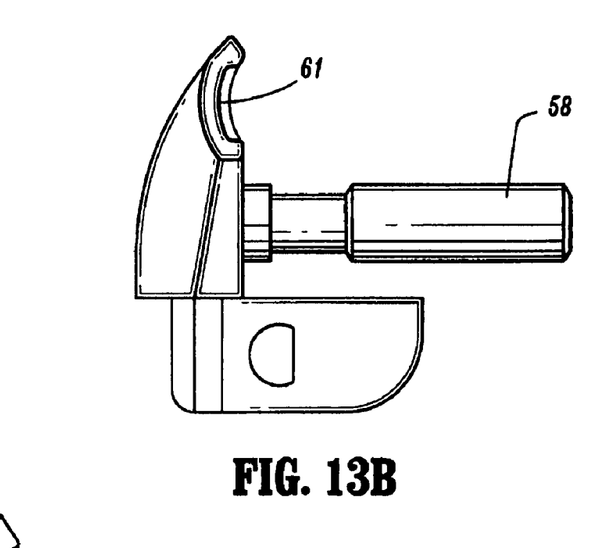
Figure 14:
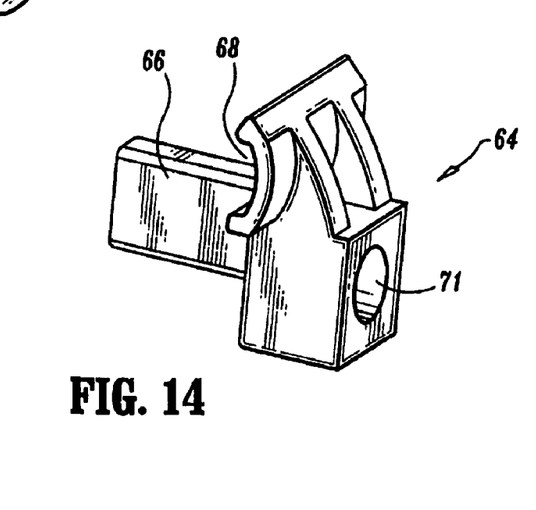
FIG. 14 is a perspective view of the movable jaw.

Referring to FIGS. 13A, 13B and 14, jaw assembly 51 includes a movable jaw 64 having an internally threaded opening 71 to receive mounting screw 58 of a stationary jaw 52. Arm 66 of movable jaw 64 is mounted within a groove 56 formed on stationary jaw 52. Ball shaft 34 is adhesively mounted within a recess (not shown) of stationary jaw 52, although other means of connection are also contemplated. A jaw approximation control member, such as locking knob 72, as best shown in FIGS. 3 and 10, is attached to a mounting screw 58 such that rotation of locking knob 72 rotates threaded mounting screw 58 to advance movable jaw 64 towards a stationary jaw 52. Spring 59 biases movable jaw 64 to the open position, away from stationary jaw 52. Approximation of jaws 52 and 64 grasps and retains instrument shaft S therebetween. Referring back to FIG. 2, in conjunction with FIGS. 13A, 13B and 14, a pair of friction enhancing members such as rubber pads 54 and 69 are mounted within grooves 61 and 68 formed on stationary jaw 52 and movable jaw 64, respectively, to facilitate atraumatic grasping of instrument shaft S.

In use, instrument shaft S is placed between movable jaw 64 and stationary jaw 52 with the jaws in the open position as shown in FIG. 2. Knob 72 is rotated to close the jaws 64, 52 to clamp and securely hold instrument shaft S. Jaw assembly 51 is manually movable to position the instrument shaft S at the desired angle relative to base 50 as ball 32 pivots within socket 15 of neck 19. Once pivoted to a desired position, for example, the position shown in FIG. 11 or FIG. 12 (other positions are clearly contemplated), locking screw handle 38 is rotated to advance locking screw 36 against ball 32 to lock ball 32 in place. This prevents further movement of the jaw assembly 51.

Figure 15:
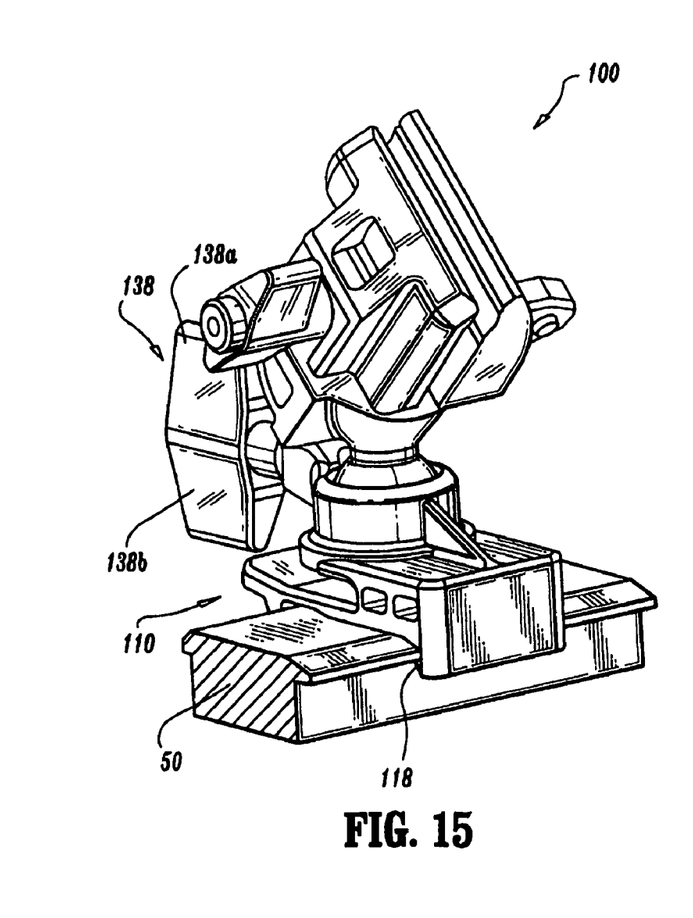
FIG. 15 is a perspective view of an alternative embodiment of an instrument holder constructed in accordance with the present disclosure.
Figure 16:
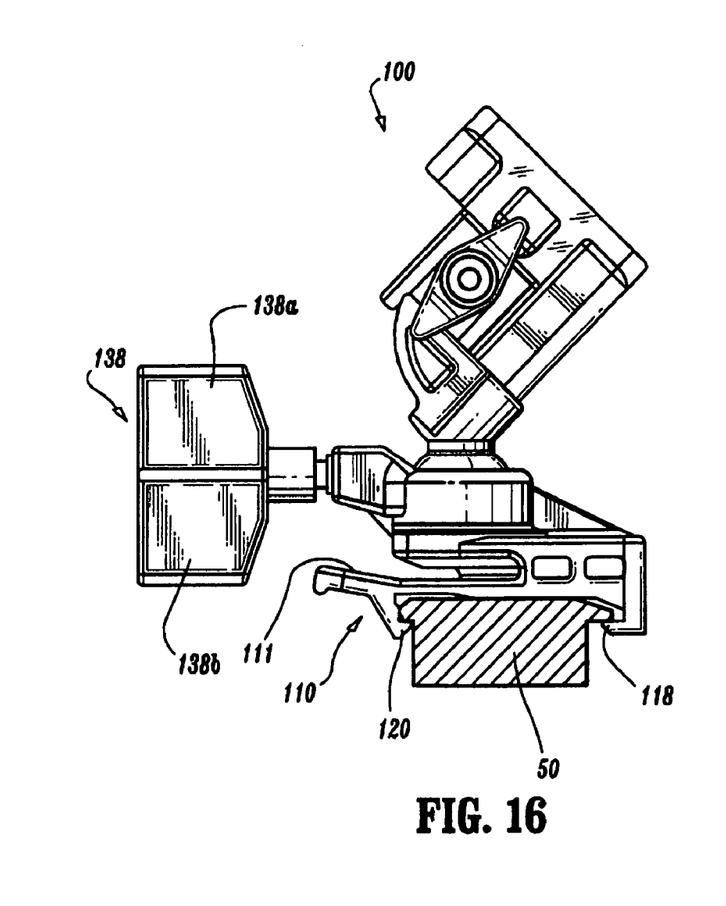
FIG. 16 is a side view of the instrument holder embodiment of FIG. 15.

Referring to FIGS. 15 and 16, an alternative embodiment of the presently disclosed apparatus for holding instruments is designated as instrument holder 100. Instrument holder 100 is similar to instrument holder 1. Therefore, the following description will only focus on those aspects of instrument holder 100 which differ from instrument holder 1. In contrast to base mounting assembly 10 of instrument holder 1, instrument holder 100 includes a mounting portion, such as a base mounting assembly 110 which is in the form of a clip having first and second lips 118, 120 which extend from a bottom surface of mounting assembly 110. Mounting assembly 110 is preferably fabricated from flexible material and includes a cantilevered extended portion 111 which deflects upon the application of a generally vertically directed force. Thus, in order to mount instrument holder 110 to base 50, lip 118 is fitted over the inner rim of base 50 and instrument holder 100 is moved into closer approximation with base 50 so that lip 120 cams outwardly and flexes extended portion 111 upwardly until lip 120 passes over the outer edge of base 50 and snaps back to its normal configuration as shown in FIG. 16. Once positioned on base 50, instrument holder 100 functions in the same way as instrument holder 1 described above to retain surgical instruments therein.

Another difference between instrument holder 100 and instrument holder 1 is the configuration of the locking knob. In particular, screw handle 38 of instrument holder 1 is in the form of a rotatable lever whereas screw handle 138 of instrument holder is in the form of a wing having extended portions 138a and 138b extending radially outwardly from the center along a plane.

It will be understood that various modifications may be made to the embodiments of the apparatus for holding surgical instruments shown and described herein. Therefore, the above description should not be construed as limiting, but merely as examples of preferred embodiments. Those skilled in the art will envision other modifications within the scope and spirit of the present disclosure.

What is claimed is:

1. An apparatus for holding a surgical instrument relative to a base, which comprises:
   a mounting portion having a first section and a second section, at least one of the sections being movable relative to the other of the sections to selectively engage portion of the base;
   a jaw assembly having first and second jaw members which define a retaining area therebetween which is configured and dimensioned to receive a shaft of the surgical instrument, the jaw assembly movably disposed relative to the mounting portion to facilitate selective positioning of the surgical instrument within a surgical site; and
   an instrument position adjustment mechanism that facilitates rotational and pivotable movement of the jaw members about the mounting portion.

2. An apparatus for holding a surgical instrument relative to a base according to claim 1 wherein at least one of the sections of the mounting portion includes a flange for engaging a rim portion of the base.

3. An apparatus for holding a surgical instrument relative to a base according to claim 1 wherein the mounting portion includes a spring for biasing the first and second sections of the mounting portion against one another to facilitate engagement of the mounting portion with the base.

4. An apparatus for holding a surgical instrument relative to a base according to claim 1 wherein the jaw assembly includes a jaw approximation control member which controls movement of at least one of the jaw members relative to the other jaw member to selectively fix the length of the surgical instrument relative to the base.

5. An apparatus for holding a surgical instrument relative to a base according to claim 4 wherein the jaw approximation control member is rotatable.

6. An apparatus for holding a surgical instrument relative to a base according to claim 1 wherein the instrument position adjustment mechanism includes an adjustment member for moving the jaw assembly relative to the mounting portion.

7. An apparatus for holding a surgical instrument relative to a base according to claim 6 wherein the adjustment mechanism further includes a lock member for selectively locking the jaw assembly relative to the mounting portion.

8. An apparatus for holding a surgical instrument relative to a base according to claim 7 wherein the lock member is rotatable.

9. An apparatus for holding a surgical instrument relative to a base according to claim 6 wherein the adjustment mechanism includes a ball which facilitates rotational and pivotable movement of the jaw member about the mounting portion.

10. An apparatus for holding a surgical instrument relative to a base according to claim 1 wherein the mounting portion includes a pair of flanges, the flanges being disposed in an inwardly-facing manner relative to the mounting portion to facilitate mounting of the apparatus to the base.

* * * * *